United States Patent [19]

Trimmer et al.

[11] Patent Number: 4,529,704
[45] Date of Patent: Jul. 16, 1985

[54] DEVICE AND METHOD FOR PREPARATION OF A CONTROL SOLUTION FOR KETONE DETERMINATION.

[75] Inventors: Robert W. Trimmer; William I. White, both of Elkhart, Ind.

[73] Assignee: Miles Laboratories, Inc., Elkhart, Ind.

[21] Appl. No.: 324,779

[22] Filed: Nov. 25, 1981

Related U.S. Application Data

[63] Continuation of Ser. No. 90,926, Nov. 5, 1979, abandoned.

[51] Int. Cl.$^3$ .............................................. G01N 33/64
[52] U.S. Cl. ........................................ 436/14; 422/56; 436/128; 562/508; 562/577
[58] Field of Search ............... 436/128, 14, 130, 166; 422/55-58; 562/508, 577

[56] References Cited

U.S. PATENT DOCUMENTS

| | | | |
|---|---|---|---|
| 3,912,655 | 10/1975 | Shukla et al. | 422/56 X |
| 3,955,926 | 5/1976 | Fischer | 422/56 X |
| 4,030,885 | 6/1977 | Das . | |
| 4,132,768 | 1/1979 | Ui et al. . | |
| 4,172,049 | 10/1979 | Pfeil et al. . | |
| 4,193,766 | 3/1980 | Daunora et al. . | |

FOREIGN PATENT DOCUMENTS

| | | | |
|---|---|---|---|
| 1209725 | 10/1970 | United Kingdom | 562/577 |
| 2002516 | 2/1979 | United Kingdom | 252/408 |

OTHER PUBLICATIONS

Hendrickson et al., "Organic Chemistry—3rd Edition", McGraw-Hill Book Co., 1970, pp. 520, 521,532,533, Examiner's personal book.
Nash et al., *Lancet*, vol. 266, Apr. 1954, pp. 801–804, "Clinical Tests for Ketonuria".

*Primary Examiner*—Arnold Turk
*Attorney, Agent, or Firm*—Edward H. Gorman, Jr.

[57] ABSTRACT

A device for preparing a control solution for ketone analysis is disclosed, as well as a method for preparing it. The device comprises a carrier vehicle incorporated with an ester of a β-ketoalkanoic acid, and a hydrolyzing substance capable of converting the ester to the corresponding β-ketoalkanoic acid. The ester has the structure

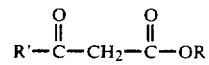

in which R is a lower alkyl group and R' is an aliphatic or cyclic group having 1 to about 7 carbon atoms. The method comprises contacting a predetermined volume of solvent with the device.

17 Claims, 1 Drawing Figure

HYDROLYSIS OF METHYLACETOACETATE

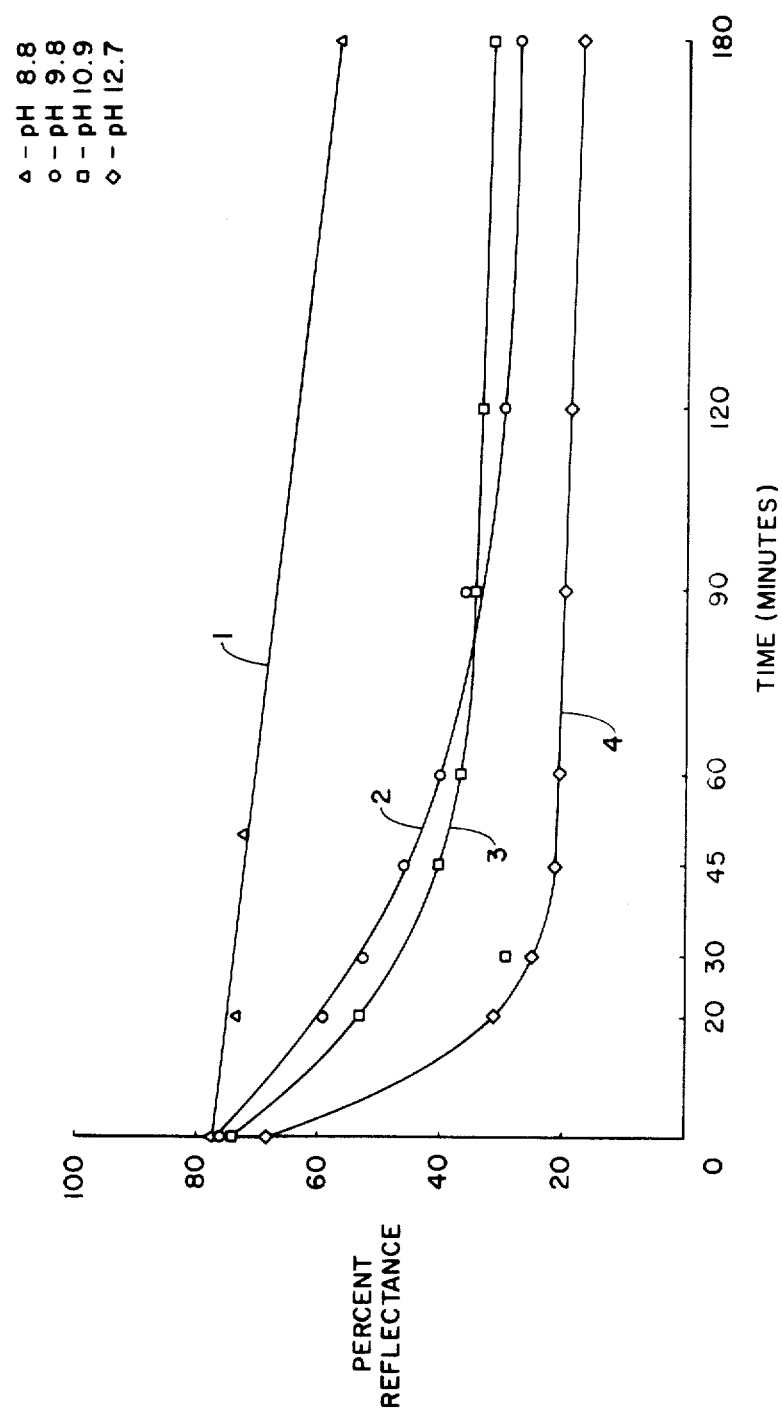

DEVICE AND METHOD FOR PREPARATION OF A CONTROL SOLUTION FOR KETONE DETERMINATION.

RELATED APPLICATION

The present application is a continuation of U.S. patent application Ser. No. 90,926, filed Nov. 5, 1979, which latter application is now abandoned.

BACKGROUND OF THE INVENTION

1. Field of the Invention

When a procedure is devised for determining the presence of a sample constituent—be the devised procedure gravimetric, volumetric, spectrophotometric or whatever mode—its efficacy in producing reliable results must somehow be assessed. Otherwise, the data developed is meaningless. Hence, devising such a procedure extends far beyond building a machine, formulating reagents or developing a technique. It also must of necessity include evaluating experimental error. There must be a way of predicting the dependability of the data produced by the procedure.

The easiest, most direct way to study parameters such as reproducibility, sensitivity, accuracy and need for calibration is to subject the procedure to a test sample wherein the analyte presence and/or concentration is known beforehand, i.e., a control solution. The data furnished by the procedure can then be compared with known data and any discrepancies properly noted.

The present invention concerns itself with assessing procedures for determining the presence and/or concentration of ketone bodies in a liquid sample. Moreover, it relates to a device for preparing a ketone control solution for use in assessing the performance of various ketone body determination procedures.

2. Description of the Prior Art

Acetoacetic acid (acetylacetic acid) is a normal end product of fatty acid oxidation in the liver. It is also produced to a very limited extent by oxidative breakdown of leucine, phenylalanine, and tyrosine. β-hydroxybutyric acid is formed from acetoacetic acid by reversible reduction. Acetone is produced through non-reversible decarboxylation of acetoacetic acid.

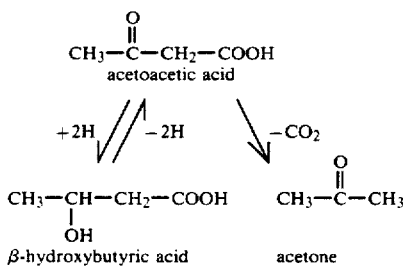

These three substances are commonly referred to as ketone bodies or acetone bodies.

Abnormally high amounts of ketone bodies in urine or blood are referred to as ketonuria and ketonemia, respectively. These conditions can occur as a result of such diverse pathological conditions as diabetes mellitus and starvation. Because of this disease/sympton relationship, especially with diabetes mellitus, there is keen interest in the determination of ketone bodies in urine. In the case of a diabetic, the detection of ketonuria is of great significance, since a change in insulin dosage or other disease management is often indicated. Thus, strong emphasis has been placed by the medical profession on ketone body analysis, resulting in the development of a plurality of procedures sensitive to the presence and/or concentration of ketone bodies in urine.

But interest in monitoring the presence of ketones is by no means restricted to the medical profession. These compounds find a myriad of industrial applications—they are used as solvents in nitrocellulose coatings and vinyl films, they find applications in paint removers, cleaning fluids, organic synthesis, explosives manufacture, and as food additives—and in each there is a need at one time or another to perform an analytical procedure to determine ketone presence and/or concentration. These and numerous other concerns with respect to ketone presence have engendered many ketone tests.

One such test takes advantage of the propensity of ketones to react with sodium nitroprusside to give intense colors. Thus, acetone when treated with nitroprusside produces an intense red-yellow color which changes to pink-violet on acidification with acetic acid [Fritz Feigl, *Spot Tests in Organic Analysis*, 7th ed. (1966)]. This phenomenon occurs as a result of a coupling reaction through the NO group of the nitroprusside and the ketone to yield an isonitrosoketone which remains in the reaction mixture as a complex, colored anion. The iron (III) of the nitroprusside is reduced to its divalent state (II). It has been found that ketones which do not contain methyl or methylene groups bound to carbonyl groups are not reactive, or at least they do not produce colorforms, with nitroprusside.

The same or similar chemistry can be found in the ketone-sensitive portion of analytical reagent strips known as N-MULTISTIX ® and KETO-DIASTIX ® and in the reagent tablet, ACETEST ®, all of which are marketed by the Ames Division of Miles Laboratories, Inc. All three of these devices for determining ketone bodies are based on the nitroprusside-ketone complexing phenomenon. Thus, when the reagent strips are immersed in an aqueous ketone solution, or when the tablet is contacted with such a solution, the formation of a colored complex indicates the presence of a ketone. Moreover, the concentration of ketone can be estimated based on the intensity and hue of the color formed.

These and other methods for ketone body estimation require, as stated supra, a way of estimating their accuracy, as well as the competency of the person performing the test. One such approach is the use of a reference sample or control—a test sample in which the chemical composition and physical characteristics simulate the test samples to be analyzed. Hence, a control can be a urine sample which has been kept in the frozen state, or perhaps it comprises pooled urine which has been concentrated through freeze drying, later to be diluted to a predetermined volume.

Exemplary of a commercially available control is TEK-CHEK ®, marketed by the Ames Division of Miles Laboratories, Inc., which utilizes the effect of a certain pH indicator in the presence of the buffering substance used in commercially available reagent strips having ketone-responsive reagent areas. Using this ketone substitute, TEK-CHEK produces a control solution which yields a positive test for ketones with the following Ames Division products: BILI-LABSTIX ®, LABSTIX ®, KETO-DIASTIX ®, KETOSTIX ®, MULTISTIX ®, N-MULTISTIX ® and ACETEST ®. TEK-CHEK is described in product literature available from the Ames Division as comprising lyophilized urine containing a chemical substance for ketones. A substitute is used because ketones are difficult to retain in their natural state. Hence, TEK-CHEK utilizes a pH indicator to simulate a urine containing pathological amounts of ketone bodies.

Other commercially available ketone control solution products are marketed by Warner-Lambert Pharmaceutical Co. and American Hospital Supply Co., both of which products are liquids and both of which employ acetone as active agent for ketone. Another product is KovaTrol available from I.C.L. Scientific of Fountain Valley, Calif., which product must be refrigerated until use.

U.S. Pat. No. 3,920,400, issued to Scheibe, et al., discloses a uric acid standard solution wherein a lithium salt of uric acid is employed as the control substance, and a complexing agent for polyvalent metals in their higher oxidation states is also present. Typical complexing agents are specified to be malonic acid, salicylic acid, oxalic acid, glutathione, cysteine, 8-oxyquinoline and ethylenediaminetetraacetic acid. The purpose of the complexing agent additive is to stabilize and prevent the decomposition of uric acid while in solution.

Still another example of a control is that disclosed in U.S. Pat. No. 3,920,580, issued to Mast and assigned to the present assignee. There is disclosed a liquid control for glucose determination in blood or serum. It comprises water, glucose and an antidiffusing agent comprising a hydrophilic polymer.

Certain salts of cholesterol hemisuccinate are described as being useful for cholesterol controls in U.S. Pat. No. 3,859,047.

U.S. patent application Ser. No. 959,693, filed Nov. 13, 1978, and assigned to the present assignee, and which issued as U.S. Pat. No. 4,193,766 on Mar. 18, 1980, is directed to a device for preparing ketone control solutions utilizing certain metal ion complexes of acetylacetone and its homologs as a substrate. See also German Offenlegungschrift No. 27 21 681, published Nov. 13, 1978. Whereas some ketone-sensitive reagents will not respond to such acetylacetonates, other, less specific ones will. It is with the latter ketone reagents that acetylacetonates find their ability as control substrates.

To summarize the state of the art prior to the present invention, numerous control solution ingredients are known. TEK-CHEK solutions provide a substitute for ketones, a known pH indicator, which reacts with the buffering substances used in various ketone-responsive chemistries normally used in ketone determinations. Other control are equally known, such as for uric acid, glucose, cholesterol, and many others. Several liquid systems are presently marketed which contain acetone. None of the prior art controls, however, makes known the concept presently disclosed and claimed. None discloses a ketone control device which utilizes the combination of a β-ketoalkanoic acid ester and alkaline substance as disclosed herein.

The present invention departs from the state of the art in dramatic fashion. No longer is it necessary to employ liquid formulations containing acetone or other liquid ketone. The present invention utilizes as an active ingredient a dry, easily storable material which, when dissolved, is directly reactive with the reagents of a ketone-sensitive test. Moreover, the invention produces a β-ketoalkanoic acid in situ. The invention eliminates the need for liquid reagents and/or substitutes for ketones such as pH indicators responsive to the buffer of the ketone-sensitive reagent system. Thus, the invention provides a dry device, one which is stable upon storage and easily handled, and which provides ketone control solutions of remarkably accurate concentrations, ergo reproducibility with the ketone-sensitive test procedure.

SUMMARY OF THE INVENTION

Briefly stated, the present invention comprises a device for preparing a control solution for ketone analysis and a method for using it. The device comprising a carrier vehicle incorporated with an ester of a β-ketoalkanoic acid, and a hydrolyzing substance capable of converting the ester to the corresponding β-ketoalkanoic acid. The ester has the structure

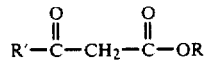

in which R is a lower alkyl group and R' is an aliphatic or cyclic group having 1 to about 7 carbon atoms. The method comprises contacting a predetermined volume of solvent with the device.

DETAILED DESCRIPTION OF THE INVENTION

As used herein, the term "carrier vehicle" is intended to include any means suitable for transporting a specified amount of the ester and hydrolyzing substance. It includes a capsule, such as a gelatin capsule, capable of dissolving in water or otherwise openable to release its contents. It can comprise a perforated capsule such that solvent can enter the capsule when in use, and leach out the ingredients contained inside. It can also comprise foil or other material made into a sealed, easily openable package, the ester and hydrolyzing substance being sealed inside until eventual use, whereupon the package is opened and its contents emptied into a predetermined volume of water. Moreover, the carrier vehicle can also comprise a carrier matrix comprising a wide range of materials. The carrier matrix is incorporated with the metal ion ester and hydrolyzing substance and, when used, is immersed in a predetermined volume of water for a predetermined time, and removed, leaving the ingredients behind in solution.

When a carrier matrix is utilized it can comprise any substance capable of being incorporated with the ingredients. Thus the matrix can take on many known forms such as those utilized for reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the paper with part of a reagent system and impregnating the meshwork with other potentially incompatible reagents. French Pat. No. 2,170,397 teaches the use of carrier matrices having greater than 50% polyamide fibers therein. Another approach to carrier matrices is disclosed in U.S. Pat.

No. 4,046,513 wherein the concept of printing reagents onto a suitable carrier matrix is employed. U.S. Pat. No. 4,046,514 discloses the interweaving or knitting of filaments bearing reagents in a reactant system. All such carrier matrix concepts can be employed in the present invention, as can others. Preferably the carrier matrix comprises a bibulous material, such as filter paper, whereby a solution of the ester and hydrolyzing substance is used to impregnate the matrix. It can also comprise a system which physically entraps these ingredients, such as polymeric microcapsules, which then rupture upon contact with the test sample. It can comprise a system wherein the ingredients are homogeneously combined with the carrier matrix in a fluid or semi-fluid state, which later hardens or sets, thereby entrapping the ingredients.

As stated supra, the ester of the present invention comprises one of a $\beta$-ketoalkanoic acid. In the structure of the ester depicted above wherein R is defined as being "lower alkyl", that term is meant to include alkyl groups having from 1 to about 6 carbon atoms, including methyl, ethyl, n-propyl, isopropyl, cyclopropyl, n-butyl, sec-butyl, tert-butyl, isobutyl, cyclobutyl, and all pentyl and hexyl isomers. R', on the other hand, can take on much broader significance. It can comprise an aliphatic group or a cyclic group having 1 to about 7 or more carbon atoms. These can be saturated, unsaturated, aromatic, substituted or unsubstituted. Especially suitable for the present invention are such esters as methyl acetoacetate, ethylacetoacetate and ethyl 3-keto-4-phenylbutyrate. Still others are 1,10-di(acetoacetyl)decane, ethyl 2-methylacetoacetate, and ethyl p-fluorobenzyl acetate. Many additional $\beta$-ketoalkanoic acid esters are within the scope of the present invention, the only limiting requisites being that the ester is hydrolyzable in the presence of the hydrolyzing substance to produce the corresponding $\beta$-ketoalkanoic acid.

Likewise, the hydrolyzing substance embraced by the present invention is intended as being broad in scope. As used herein, "hydrolyzing substance" is intended to mean acids or bases of suitable strength to hydrolyze the ester. Some acids suitable for this purpose are the toluene sulfonic acids, benzene sulfonic acids, sulfosalicylic acid, and the naphthalene disulfonic acids and others. Basic substances, on the other hand, are the preferred hydrolyzing substances. These include among others, such substances as potassium carbonate, sodium carbonate, sodium hydroxide, potassium hydroxide, and mixtures thereof, including mixtures of sodium bicarbonate and said substances.

The feature mainly determinative in selecting the hydrolyzing substance is the ultimate pH produced in solution. If a base is to be used, too low a pH will preclude hydrolysis of the ester or will effect too slow a rate of hydrolysis. It has been found that an alkaline substance should be basic enough or present in sufficient amounts to provide a pH of at least about 10.

Reference to the drawing reveals the alkaline pH dependence of the hydrolysis of methyl acetoacetate, a preferred ester for use in the present invention. The graph depicts the amount of ester hydrolysis with respect to time for aqueous solutions of methyl acetoacetate at a concentration of 0.150 grams per deciliter (g%) at pH's of 8.8, 9.8, 10.9 and 12.7. The data shows that hardly any hydrolysis to acetoacetic acid occurred at pH 8.8 even after three hours, whereas almost complete hydrolysis took place after 30 minutes at pH 12.7. Significant hydrolysis began to occur at pH 9.8. This data shows the threshold criticality of about pH 10 for significant hydrolysis, ergo generation of ketone body substrate for a control solution.

Given the theoretical and experimental considerations of the present teachings, selection of the proper hydrolyzing substance becomes determinative through routine laboratory experimentation. All one need do is incorporate the ester and hydrolyzing substance in a carrier vehicle as shown herein and prepare a control solution. The generation of the $\beta$-ketoalkanoic acid can then be followed by spectrophotometric or other means known in the art. Too little generation of the keto acid is indicative of insufficient hydrolyzing agent, i.e., generation of a pH insufficient to hydrolyze the ester.

The amount of $\beta$-ketoalkanoic acid ester utilized in the present invention, i.e., incorporated with the carrier vehicle, depends upon several parameters. Firstly, the particular system in which ketone body presence might be of analytical interest demands an analytical system responsive to a certain range of ketone concentration. This concentration range will vary from system to system. Pathological urines, for example, necessitate that the ketone-sensitive area of N-MULTISTIX be responsive to ketone concentrations of from about 3 up to about 160 milligrams per deciliter (mg%). Accordingly, for a device for preparing a control solution for N-MULTISTIX reagent strips, an amount of ester sufficient to provide a color change indicative of ketone concentrations in that range is required.

A second determining factor is the volume of control solution the device will ultimately be used to prepare. Thus if the device is incorporated with amounts of ingredients which when contacted with 30 milliliters of water will provide the desired N-MULTISTIX reagent strip response, that same device will provide too strong a response with 12 milliliters of water and too weak a response with one liter. Suffice it to say that the amount of ester incorporated with the carrier vehicle must be at least sufficient to provide the desired ketone concentration range in a predetermined amount of solvent. In urinalysis procedures, that concentration range is from about 0.1 to about 160 millimoles per liter.

In another embodiment of the invention, the carrier vehicle is incorporated with the sodium enolate derivative of the ester. For example, it is well known that most alcohols react with metals such as sodium to form alkoxides. The latter compounds are extremely reactive with water to yield the alcohol and the hydroxide of the metal. This is represented by

  (1)

  (2)

In the case of $\beta$-ketoalkanoic acid esters, the phenomenon of keto-enol tautomerism gives rise to the following reaction sequence

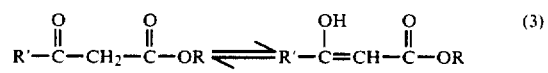  (3)

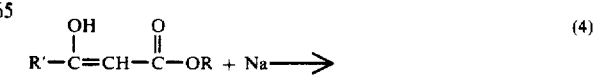  (4)

-continued

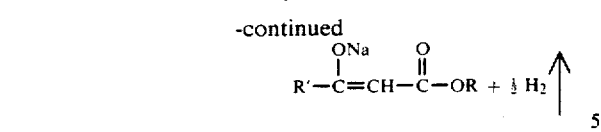

(5)
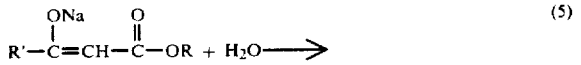

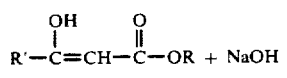

(6)
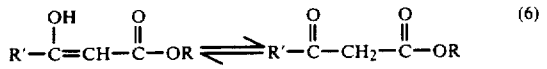

When equations 5 and 6 are considered additively, the net reaction is (7)

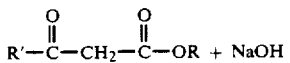

Equation 7 shows that the sodium alkoxy derivative of a β-ketoalkanoic acid ester is converted to the ester and sodium hydroxide upon the addition of water. This reaction is extremely rapid and substantially irreversible. Thus, for the purposes of the present invention, the alkali metal derivative of a β-ketoalkanoic acid ester is considered to be synonymous with the combination of the ester and a hydrolyzing substance capable of hydrolyzing the ester to form the corresponding β-ketoalkanoic acid. This can be easily visualized when the right side of equation 7 is taken one step further, viz.

(8)
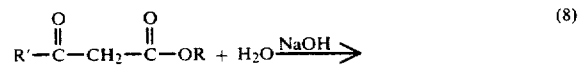

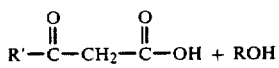

Thus, the composition can comprise an alkali metal enolate having the structure

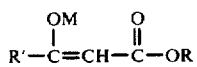

wherein R' and R are as defined, supra, and M is an alkali metal ion. Some compounds included by this structure are ethyl acetoacetate sodium salt (Aldrich Chemical Co.), and methyl acetoacetate sodium salt. M can be lithium, sodium, potassium, and rubidium.

In a preferred method for preparing the test device, filter paper is sequentially impregnated with the hydrolyzing substance and ester. Thus, a strip of filter paper is immersed in an aqueous solution of the hydrolyzing agent, dried, immersed in an alcoholic solution of the ester and redried. With the paper matrix thus incorporated with the ingredients, it is then attached to a rigid or semi-rigid support such as polystyrene film. A double-faced adhesive tape has been found especially suitable for this purpose. Before mounting, the impregnated paper is cut into narrow strips. These are mounted on polystyrene film along one edge using the double-faced adhesive. The filter paper/polystyrene composite is then slit along lines perpendicular to the axis of the filter paper, thus providing an oblong polystyrene strip having a piece of impregnated filter paper at one end, the other end serving as a handle.

EXAMPLES

The following Examples are provided to further illustrate preferred embodiments of the invention presently disclosed and claimed. As such, they are meant as being illustrative, and are not intended, nor are they to be construed, as limiting the scope of the claims appended hereto.

EXAMPLE I

Hydrolysis of Methyl Acetoacetate at Various pH Levels

An experiment was conducted to study the hydrolysis behavior of methyl acetoacetate under different pH conditions. Specifically, solutions of methyl acetoacetate were prepared in aqueous buffers. Each solution was monitored at regular time intervals for the appearance of acetoacetate. The results plotted in FIG. 1 show that significant ester hydrolysis did not take place until a pH of at least 9.8 was achieved.

Four buffered solutions were used in this experiment having pH's of 9, 10, 11 and 13, respectively. The pH 9 buffer was obtained from Fisher Scientific Supply Company, Catalogue No. SO-B-114. It comprises a boric acid-potassium chloride-sodium hydroxide solution in water. The pH 10 buffer was obtained from J. T. Baker Chemical Company as Borate Buffer Solution No. 1-5609. The pH 11 buffer was prepared from a 1M $K_2CO_3$ solution in distilled water by adding 1N HCl until a pH of 11 was indicated by a pH meter. The pH 13 solution was 0.1N NaOH.

To a 100 ml aliquot of each buffer was added 0.15 grams of methyl acetoacetate. The resultant solutions had final pH values of 8.8, 9.8, 10.9 and 12.7, respectively, the slight lowering of pH from those of the original buffers being attributed to the ester addition. The reaction was followed using filter paper pads impregnated with a ketone-sensitive reagent system which yielded a pink color in the presence of acetoacetate, but which did not color in response to the nonhydrolyzed ester. Such a system is fully described in U.S. Pat. No. 4,147,514, which patent is incorporated herein by reference. Color formation was followed using a spectrophotometer responsive to reflected light at 580 and 720 nanometers. The reagent pads had been previously calibrated by measuring percent reflectance of acetoacetate solutions having known concentrations. The data obtained is set forth in the Table.

TABLE

| Buffer pH | Time (min.) | % Reflectance | Acetoacetate (mg %) |
|---|---|---|---|
| 8.8 | 0 | 77.8 | 0 |
|  | 20 | 73.5 | 1 |
|  | 50 | 72.0 | 1.2 |
|  | 180 | 57.3 | 9.0 |
| 9.8 | 0 | 75.9 | 0.5 |
|  | 20 | 59.4 | 8.0 |
|  | 30 | 53.4 | 12.5 |
|  | 45 | 46.0 | 21.0 |
|  | 60 | 40.4 | 23.5 |
|  | 90 | 35.1 | 37.5 |
|  | 120 | 30.2 | 49.0 |
|  | 180 | 27.6 | 59.0 |
| 10.9 | 0 | 74.1 | 1.0 |

TABLE-continued

| Buffer pH | Time (min.) | % Reflectance | Acetoacetate (mg %) |
|---|---|---|---|
| | 20 | 53.7 | 12.0 |
| | 30 | 28.8* | 54.0* |
| | 45 | 39.9 | 30.0 |
| | 60 | 36.7 | 35.0 |
| | 90 | 34.4 | 38.0 |
| | 120 | 33.6 | 40.0 |
| | 180 | 31.6 | 45.0 |
| 12.7 | 0 | 68.5 | 2.0 |
| | 20 | 31.6 | 45.0 |
| | 30 | 25.7 | 65.0 |
| | 45 | 21.4 | 93.0 |
| | 60 | 21.4 | 93.0 |
| | 90 | 19.5 | 115.0 |
| | 120 | 19.0 | 120 |
| | 180 | 18.6 | 125 |

*anomalous reading

Curve 1 of the FIGURE is a plot of the above data at pH 8.8. As can be seen, little hydrolysis (<8% of theoretical yield) took place, even after three hours. Curves 2, 3 and 4 on the other hand, manifest significant hydrolysis of the ester, i.e., formation of acetoacetate, after only 20 minutes. Moreover, as the pH was increased from 9.8 to 12.7 (curves 2, 3, and 4, respectively) the rapidity and extent of ester hydrolysis is increased accordingly.

EXAMPLE II

Preparation of a Preferred Device

An experiment was conducted to prepare devices for use in the preparation of a ketone control solution. Each device comprised a square of filter paper mounted on one end of a polystyrene strip. The paper was impregnated with potassium carbonate and methylacetoacetate.

A strip of Eaton and Dikeman No. 222 filter paper measuring about two inches by ten inches was immersed in a 2.54M (35 grams per deciliter) solution of $K_2CO_3$ in distilled water, removed when completely saturated and dried in an air oven at about 70° C. for 15 to 25 minutes. The dried paper was then immersed in a second solution containing 20 grams methylacetoacetate per 100 ml of ethanol (23A), removed and dried at 70° for 15 to 25 minutes in an air oven.

The dried, ingredient-impregnated paper was then laminated onto one side of a paper-backed double-faced adhesive tape known as Double Stick 415 (3M Company). The paper/tape composite was then attached, using the unoccupied adhesive tape face, along an edge of a sheet of axially oriented polystyrene obtained from Plastic Suppliers, Inc. The resulting laminate was then slit perpendicular to the paper strip to provide devices measuring about 3.5 inches by 0.4 inches, and having a 0.4 inch square of the impregnated paper at one end.

EXAMPLE III

Preparation of a Ketone Control Solution

An experiment was conducted to study preparation of ketone control solutions utilizing the strip device prepared in Example II, supra. A strip was immersed paper-end down into a cuvette containing 12.0 ml distilled water, being careful to incur as little agitation as possible. After 30 minutes, the strip and solution were thoroughly agitated and the strip was removed. The resultant ketone control solution had an acetoacetic acid (acetoacetate) concentration of 15 mg%.

What is claimed is:

1. A device useful in the preparation of a ketone control solution, said device comprising a carrier matrix incorporated with a predetermined quantity of a composition comprising (a) a β-ketoalkanoic acid ester having the structure

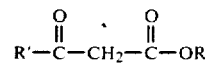

in which R is lower alkyl and R' is an aliphatic or cyclic group having 1 to about 7 carbon atoms; and (b) a hydrolyzing substance capable of converting said ester to the corresponding β-ketoalkanoic acid when said ester and substance are placed in a solvent therefor.

2. The device of claim 1 wherein R' is lower alkyl.

3. The device of claim 1 wherein R' is methyl.

4. The device of claim 1 wherein said ester is methylacetoacetate, ethylacetoacetate or ethyl 3-keto-4-phenyl butyrate.

5. The device of claim 1 wherein said ester is methylacetoacetate.

6. The device of claim 1 wherein said carrier matrix is paper.

7. The device of any of claims 1-5 wherein said hydrolyzing substance is a base.

8. The device of claim 7 wherein said base is potassium carbonate, sodium carbonate, potassium hydroxide, sodium hydroxide, or mixtures thereof.

9. The device of claim 7 wherein said base is an alkali metal carbonate.

10. A device useful in the preparation of a ketone control solution, said device comprising a carrier matrix incorporated with (a) a predetermined amount of a (lower alkyl)acetoacetate and (b) an alkaline substance capable of hydrolyzing said (lower alkyl)acetoacetate to form acetoacetic acid; and a support member comprising an elongated plastic strip having said carrier matrix affixed thereto.

11. The device of claim 13 wherein said alkaline substance is an alkali metal carbonate.

12. The device of claim 1 wherein the β-ketoalkanoic acid ester and the hydrolyzing substance are simultaneously present as a compound having the structure

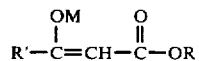

in which R is lower alkyl, R' is an aliphatic or cyclic group having 1 to about 7 carbon atoms, and M is an alkali metal ion.

13. The device of claim 12 wherein R' is lower alkyl.

14. The device of claim 12 wherein R' is methyl.

15. The device of claim 12 wherein M is Na+.

16. The device of claim 12 wherein R and R' are both methyl and M is Na+.

17. A method for preparing a ketone control solution, comprising contacting a predetermined volume of solvent with the device of any of claims 1-5, 10, 11, 13-16 or 12.

* * * * *